US008853398B2

(12) United States Patent
Mais et al.

(10) Patent No.: US 8,853,398 B2
(45) Date of Patent: Oct. 7, 2014

(54) PROCESS FOR PREPARING METHYL {4,6-DIAMINO-2-[1-(2-FLUOROBENZYL)-1H-PYRAZOLO[3,4-B]PYRIDIN-3-YL]PYRIMIDIN-5-YL} METHYLCARBAMATE AND ITS PURIFICATION FOR USE AS PHARMACEUTICALLY ACTIVE COMPOUND

(71) Applicant: Bayer Intellectual Property GmbH, Monheim (DE)

(72) Inventors: Franz-Josef Mais, Düsseldorf (DE); Joachim Rehse, Leichlingen (DE); Winfried Joentgen, Köln (DE); Konrad Siegel, Düsseldorf (DE)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 13/945,639

(22) Filed: Jul. 18, 2013

(65) Prior Publication Data

US 2013/0310563 A1  Nov. 21, 2013

Related U.S. Application Data

(63) Continuation of application No. 12/955,510, filed on Nov. 29, 2010, now Pat. No. 8,492,544.

(30) Foreign Application Priority Data

Nov. 27, 2009  (EP) ..................... 09177371

(51) Int. Cl.
C07D 403/04 (2006.01)
C07D 487/04 (2006.01)
C07D 239/50 (2006.01)
C07D 239/48 (2006.01)
C07D 471/04 (2006.01)
C07C 325/02 (2006.01)

(52) U.S. Cl.
CPC ............ C07D 471/04 (2013.01); C07D 487/04 (2013.01); *C07D 239/48* (2013.01); *C07D 239/50* (2013.01); *C07D 403/04* (2013.01); *C07C 325/02* (2013.01)
USPC ....................................... 544/328

(58) Field of Classification Search
CPC .. C07D 403/04; C07D 487/04; C07D 239/50; C07D 239/48
USPC ................................. 544/328, 329
See application file for complete search history.

(56) References Cited

U.S. PATENT DOCUMENTS 6,166,027 A   12/2000  Straub et al.
6,180,656 B1   1/2001  Furstner et al.
6,362,178 B1   3/2002  Niewohner et al.
6,693,102 B2   2/2004  Stasch et al.
6,903,089 B1   6/2005  Stasch et al.
6,919,345 B2   7/2005  Stasch et al.
7,105,523 B2   9/2006  Stasch et al.
7,115,599 B2  10/2006  Stasch et al.
7,173,037 B2   2/2007  Alonso-Alija et al.
7,291,622 B2  11/2007  Stasch et al.
7,317,016 B2   1/2008  Stasch et al.
8,420,656 B2   4/2013  Follmann et al.

(Continued)

FOREIGN PATENT DOCUMENTS

CA  2346698  4/2000
CA  2749048  7/2010

(Continued)

OTHER PUBLICATIONS

Ko et al., "YC-1, a Novel Activator of Platelet Guanylate Cyclase", Blood, 1994, 84, pp. 4226-4233.

(Continued)

*Primary Examiner* — Venkataraman Balasubramanian
(74) *Attorney, Agent, or Firm* — Buchanan Ingersoll & Rooney PC

(57) ABSTRACT

The present invention relates to a process for preparing methyl {4,6-diamino-2-[1-(2-fluorobenzyl)-1H-pyrazolo[3,4-b]pyridin-3-yl]pyrimidin-5-yl}methylcarbamate of the formula (I)

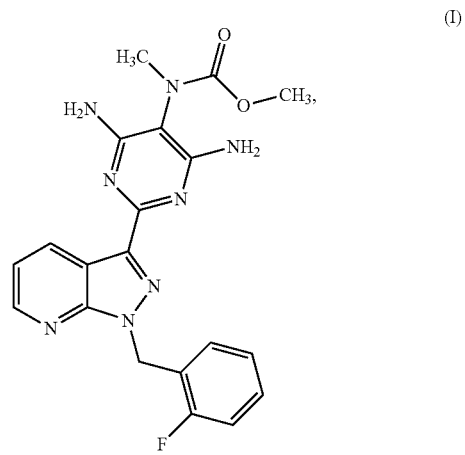

and to a process for purifying the crude product of the compound of the formula (I) for use as pharmaceutically active compound, where, for purification, methyl {4,6-diamino-2-[1-(2-fluorobenzyl)-1H-pyrazolo[3,4-b]pyridin-3-yl]pyrimidin-5-yl}methylcarbamate sulphinyldimethane (1:1), i.e. a compound of the formula (II), is isolated as intermediate or is generated as intermediate in this purification process, if appropriate present in a mixture.

4 Claims, No Drawings

(56) References Cited

U.S. PATENT DOCUMENTS

| | | | |
|---|---|---|---|
| 8,492,544 B2* | 7/2013 | Mais et al. ............... | 544/328 |
| 2004/0235863 A1 | 11/2004 | Feurer et al. | |
| 2005/0222170 A1 | 10/2005 | Welgand et al. | |
| 2006/0052397 A1 | 3/2006 | Alonso-Alija et al. | |
| 2007/0225299 A1 | 9/2007 | Bischoff et al. | |
| 2010/0029653 A1 | 2/2010 | Schirok et al. | |
| 2011/0183999 A1 | 7/2011 | Grunenberg et al. | |
| 2012/0029002 A1 | 2/2012 | Straub et al. | |

FOREIGN PATENT DOCUMENTS

| | | |
|---|---|---|
| EP | 0463756 | 4/1995 |
| WO | WO 94/28902 | 12/1994 |
| WO | WO 00/06567 | 2/2000 |

OTHER PUBLICATIONS

Mulsch et al., "Effect of YC-1, an NO-independent, Superoxide-Sensitive Stimulator of Soluble Gyanylyl Cyclase, on Smooth Muscle Responsiveness to Nitrovasodilators", Brit. J. Pharm., 1997, 120, pp. 681-689.

Goldberg et al., "Stimulation of Human Platelet Guanylate Cyclase by Fatty Acids", J. Biol. Chem., 1997, 252, pp. 1279-1285.

Pettibone et al., "A Structurally Novel Stimulator of Guanylate Cyclase with Long-Lasting Hypotensive Activity in the Dog", Euro. J. of Pharmacology, 1985, 116, pp. 307-312.

Yu et al., "Vasorelaxant Effect of Isoliquiritigenin, A Novel Soluble Guanylate Cyclase Activator, in Rat Aorta", Brit. J. of Pharmacology, 1995, 114, pp. 1587-1594.

Cavalieri et al., "A Synthesis of Adenine: The Incorporation of Isotopes of Nitrogen and Carbon", J. Am. Chem. Soc., 1949, 71, pp. 533-536.

Li et al., "Synthesis and Structure-Activity Relationships of 2-Pyridones: A Novel Series of Potent DNA Gyrase Inhibitors as Antibacterial Agents", J. Med. Chem., 1996, 39, pp. 3070-3088.

U.S. Appl. No. 13/851,373, filed in U.S. on Mar. 27, 2013.

Mittendorf et al., "Discovery of Riociguat (BAY 63-2521): A Potent, Oral Stimulator of Soluble Guanylate Cyclase for the Treatment of Pulmonary Hypertension", Chem Med Chem, 2009, No. 4, pp. 853-865.

Evans et al., "The Preparation of 4-Amino-and Other Pteridines", J. of Chem. Soc., 1956, pp. 4106-4113.

Schwoch et al., "2-3-Dihydrospirol [1 H-4 and 5-azabenzimidazole-2, 1'-cyclohexane](=Spiro[cyclohexane-1.2'(3'H)-imidazo[4,5-hb]pyridine] and Spiro[cyclohexane-1.2'(3'H)-1'H-imidaxo[4,5-c[pyridine])", Reactions with Nucleophiles, Helvetia Chimica Acta, 1994, Vo. 77, pp. 2175-2190.

Barraclough et al., "Mono-aroylation of 2,3-and 3,4-Diaminopyridine and 4,5-Diaminopyrimidine, and Syntheses of Putative Inotrope/b-Adrenoceptor Antagonists", J. Chem. Res., 1996, vol. 9, pp. 2316-2335.

* cited by examiner

PROCESS FOR PREPARING METHYL {4,6-DIAMINO-2-[1-(2-FLUOROBENZYL)-1H-PYRAZOLO[3,4-B] PYRIDIN-3-YL]PYRIMIDIN-5-YL}METHYL CARBAMATE AND ITS PURIFICATION FOR USE AS PHARMACEUTICALLY ACTIVE COMPOUND

This application is a continuation of U.S. patent application Ser. No. 12/955,510 filed on Nov. 29, 2010, which issued on Jul. 23, 2013 as U.S. Pat. No. 8,492,544 and claims benefit of priority to European Patent App. Ser. No. 09177371.3 filed on Nov. 27, 2009, all of which applications are hereby incorporated herein by reference in their entireties.

The present invention relates to a process for preparing methyl {4,6-diamino-2-[1-(2-fluorobenzyl)-1H-pyrazolo[3,4-b]pyridin-3-yl]pyrimidin-5-yl}methylcarbamate of the formula (I)

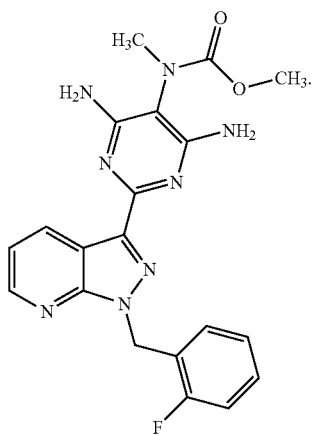

(I)

The invention furthermore relates to a process for purifying the crude product of the compound of the formula (I) for use as a pharmaceutically active compound, where, for purification, methyl {4,6-diamino-2-[1-(2-fluorobenzyl)-1H-pyrazolo[3,4-b]pyridin-3-yl]pyrimidin-5-yl}methylcarbamate sulphinyldimethane (1:1), i.e. a compound of the formula (II)

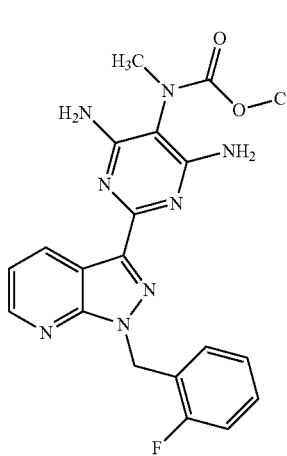

(II)

is isolated as intermediate or is generated as intermediate in this purification process, if appropriate present in a mixture.

The compound of the formula (I) acts as a stimulator of soluble guanylate cyclase and can be used as an agent for the prophylaxis and/or treatment of cardiovascular disorders such as, for example, for the treatment of high blood pressure and of heart failure, stable and unstable angina pectoris, peripheral and cardiac vascular disorders, of arrhythmias, for the treatment of thromboembolic disorders and ischemias such as myocardial infarction, stroke, transitory and ischemic attacks, disturbances of peripheral blood flow, prevention of restenoses such as following thrombolysis therapies, percutaneous transluminal angioplasties (PTA), percutaneous transluminal coronary angioplasties (PTCA), bypass and for the treatment of arteriosclerosis, asthmatic disorders and diseases of the urogenital system such as, for example, prostate hypertrophy, erectile dysfunction, female sexual dysfunction, osteoporosis, glaucoma, pulmonary hypertension, gastroparesis and incontinence.

The preparation of the compound of the formula (I) and its purification are known in principle. WO 03/095451 describes the preparation of the compound of the formula (I) by the route below.

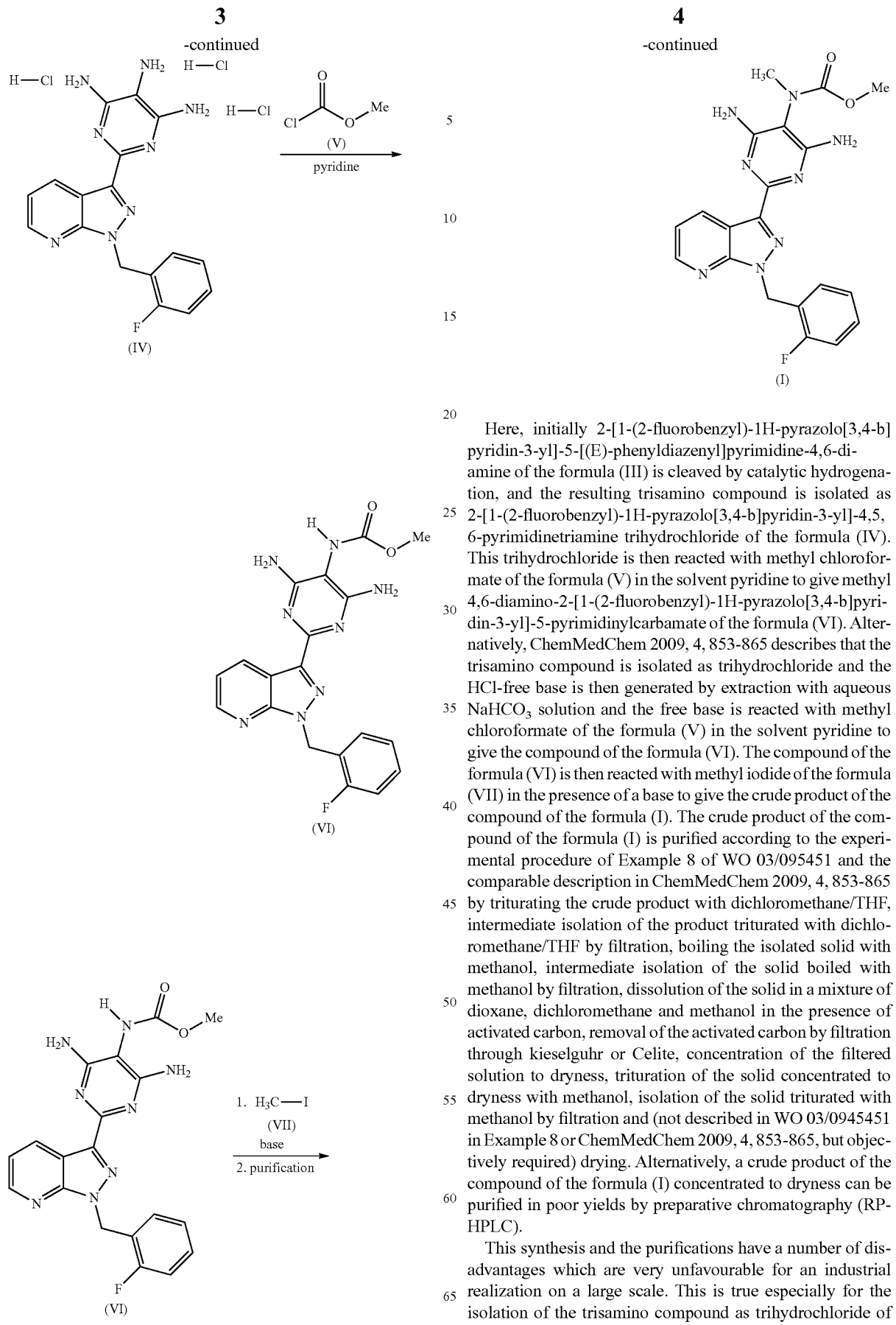

Here, initially 2-[1-(2-fluorobenzyl)-1H-pyrazolo[3,4-b]pyridin-3-yl]-5-[(E)-phenyldiazenyl]pyrimidine-4,6-diamine of the formula (III) is cleaved by catalytic hydrogenation, and the resulting trisamino compound is isolated as 2-[1-(2-fluorobenzyl)-1H-pyrazolo[3,4-b]pyridin-3-yl]-4,5,6-pyrimidinetriamine trihydrochloride of the formula (IV). This trihydrochloride is then reacted with methyl chloroformate of the formula (V) in the solvent pyridine to give methyl 4,6-diamino-2-[1-(2-fluorobenzyl)-1H-pyrazolo[3,4-b]pyridin-3-yl]-5-pyrimidinylcarbamate of the formula (VI). Alternatively, ChemMedChem 2009, 4, 853-865 describes that the trisamino compound is isolated as trihydrochloride and the HCl-free base is then generated by extraction with aqueous NaHCO₃ solution and the free base is reacted with methyl chloroformate of the formula (V) in the solvent pyridine to give the compound of the formula (VI). The compound of the formula (VI) is then reacted with methyl iodide of the formula (VII) in the presence of a base to give the crude product of the compound of the formula (I). The crude product of the compound of the formula (I) is purified according to the experimental procedure of Example 8 of WO 03/095451 and the comparable description in ChemMedChem 2009, 4, 853-865 by triturating the crude product with dichloromethane/THF, intermediate isolation of the product triturated with dichloromethane/THF by filtration, boiling the isolated solid with methanol, intermediate isolation of the solid boiled with methanol by filtration, dissolution of the solid in a mixture of dioxane, dichloromethane and methanol in the presence of activated carbon, removal of the activated carbon by filtration through kieselguhr or Celite, concentration of the filtered solution to dryness, trituration of the solid concentrated to dryness with methanol, isolation of the solid triturated with methanol by filtration and (not described in WO 03/0945451 in Example 8 or ChemMedChem 2009, 4, 853-865, but objectively required) drying. Alternatively, a crude product of the compound of the formula (I) concentrated to dryness can be purified in poor yields by preparative chromatography (RP-HPLC).

This synthesis and the purifications have a number of disadvantages which are very unfavourable for an industrial realization on a large scale. This is true especially for the isolation of the trisamino compound as trihydrochloride of the formula (IV). The addition of hydrochloric acid requires an acid-proof industrial plant, and the yield of the step is only an unsatisfactory 59.3% of theory (see, for example, Example 8A of WO 03/095451). The realization of the reaction of the trisamino compound of the formula (IV) or the corresponding HCl-free base in the solvent pyridine is likewise disadvantageous. The compound of the formula (VI) can only be isolated by complete evaporation of the reaction mixture, which is disadvantageous on an industrial scale (see, for example, Example 5 of WO 03/095451). On a relatively large scale, such steps generally result in considerable problems such as sticking-on or thermal decomposition owing to the substantially longer thermal stress when a reaction is carried out on a relatively large scale. The purification of the product of the formula (VI) according to the experimental procedure of Example 5 from WO 03/095451 by boiling in diethyl ether, too, has considerable disadvantages. Because of the high flammability of diethyl ether, this step can be realized only with increased industrial expenditure.

However, particularly disadvantageous are the purification processes for the crude product of the formula (I). An effective purification is a conditio sine qua non for use as a pharmaceutically active compound. The described purification via RP HPLC, i.e. the chromatographic purification, is a laboratory method, the realization of which on an industrial scale is very expensive. In addition, the stated yield of only 29% for the synthesis step to the crude product of the formula (I) and its purification is very low. The alternative preparation and purification method is very complicated. It comprises a total of 5 isolations of solids (2 concentrations to dryness and 3 filtrations), and, as already mentioned above, concentrations to dryness on an industrial scale are very unfavourable. Altogether, when carrying out a chemical step, a number of 5 isolations of solids for the preparation and purification of a pharmaceutically active compound on an industrial scale is very disadvantageous.

Accordingly, it was the object to provide a simplified process which is safe and can also be carried out advantageously on an industrial scale and which supports an active compound in high yield and high purity in pharmaceutically acceptable quality.

Surprisingly, we have now found a process for preparing methyl {4,6-diamino-2-[1-(2-fluorobenzyl)-1H-pyrazolo[3,4-b]pyridin-3-yl]pyrimidin-5-yl}methylcarbamate of the formula (I)

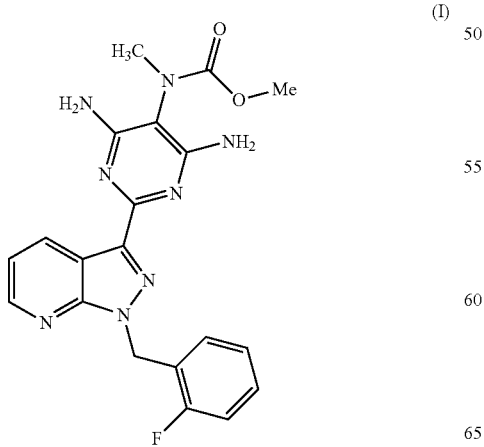

(I)

and its purification for use as a pharmaceutically active compound. This novel process and the purification of the crude product of the compound of the formula (I) differ from the processes known to date in the following points:

After catalytic hydrogenation of the compound of the formula (III), the trisamino compound is isolated as the free base of the formula (VIII) without intermediate formation of salts

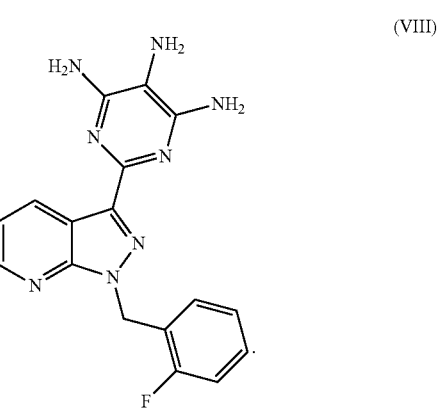 [SMILES: Nc1nc(-c2nn(Cc3ccccc3F)c3ncccc23)nc(N)c1N]

(VIII)

The preparation of the compound of the formula (VI) is carried out using methyl chloroformate or dimethyl dicarbonate as reagent in a pyridine-free process

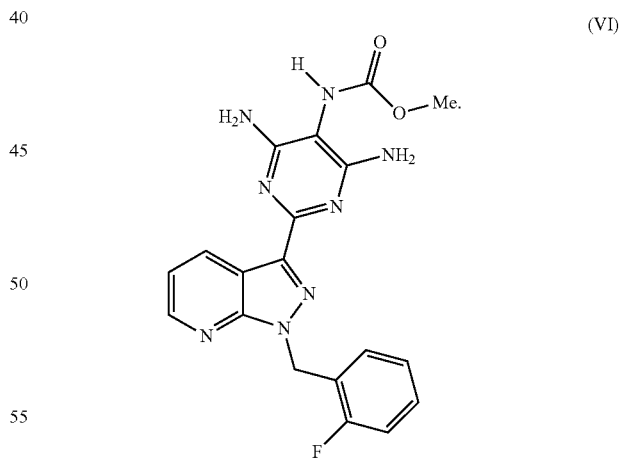

(VI)

The compound of the formula (VI) is converted in a manner known per se using a methylating agent into a crude product of the formula (I); the purification of the crude product of the formula (I) for use as pharmaceutically active compound is carried out via the compound methyl {4,6-diamino-2-[1-(2-fluorobenzyl)-1H-pyrazolo[3,4-b]pyridin-3-yl]pyrimidin-5-yl}methylcarbamate sulphinyldimethane (1:1), i.e. a compound of the formula (II) as isolated intermediate or generated in a mixture

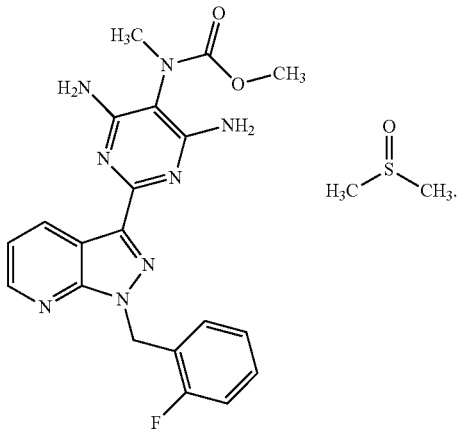

(II)

By virtue of these differences, it is possible to overcome the disadvantages of the processes known to date and to obtain an active compound in high yield and high purity and pharmaceutically acceptable quality.

The process according to the invention for preparing the compound of the formula (I) and the purification via the intermediate of the formula (II) are described in detail below.

Catalytic Hydrogenation of the Compound of the Formula (III)

The first step of the process according to the invention begins with a catalytic hydrogenation of the compound of the formula (III).

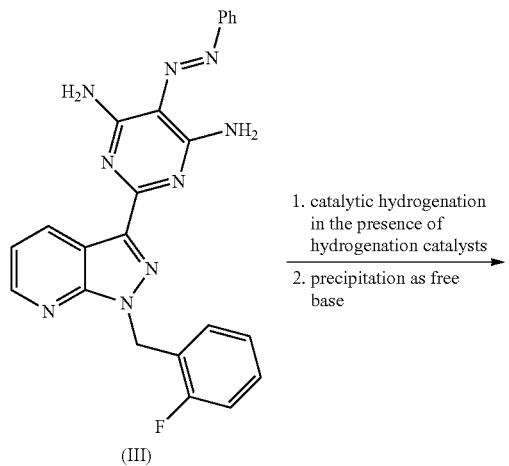

(III)

This may be carried out in the presence of Raney nickel or industrially customary Pt/carbon or Pd/carbon catalysts. Preference is given to Pt/carbon and Pd/carbon. N,N-Dimethylformamide (DMF), N,N-dimethylacetamide (DMA) or N-methyl-2-pyrrolidone (NMP), preferably DMF, serves as solvent.

Hydrogenation conditions are temperature 40-80° C., preferably 50-70° C., pressure: 2-90 bar, preferably 5-70 bar, of hydrogen, hydrogenation time: 1-72 h, preferably 3-36 h.

After removal of the catalyst by filtration, the product is precipitated from a $C_1$-$C_4$-alcohol, preferably methanol or ethanol, and/or water. Preference is given to a mixture of methanol, isopropanol or ethanol and water.

In the context of the invention, a $C_1$-$C_4$-alcohol is a straight-chain or branched alcohol having 1 to 4 carbon atoms. The following may be mentioned by way of example and by way of preference: methanol, ethanol, n-propanol, isopropanol, n-butanol and tert-butanol. This definition also applies to the $C_1$-$C_4$-alcohols used hereinbelow.

It is also possible to remove some of the solvent prior to the precipitation, a partial distillative removal of 0-80%, preferably 40-70%, of the solvent is in accordance with the invention.

The moist product obtained in this manner is dried under reduced pressure: this gives the product of the formula (VIII) (corresponds to the free base of the formula (IV)).

Reaction of the Compound of the Formula (VIII) with Methyl Chloroformate (V)

The product of the formula (VIII) is then reacted, for example, with methyl chloroformate of the formula (V) in a novel pyridine-free process to give the product of the formula (VI).

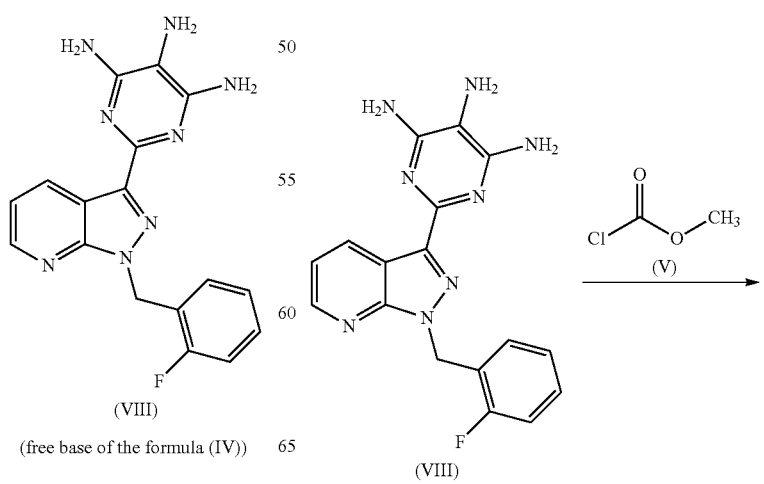

(VIII)
(free base of the formula (IV))

(VIII)

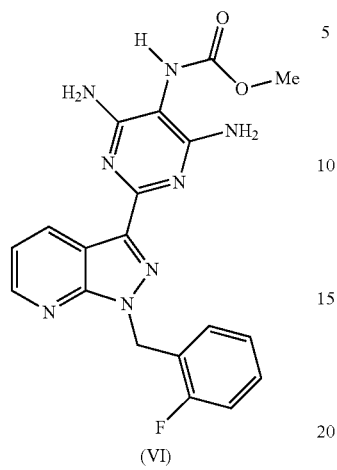

(VI)

The solvent used for the reaction is a $C_1$-$C_4$-alcohol, preferably ethanol, methanol, isopropanol, particularly preferably isopropanol.

The amount of methyl chloroformate is from 1.0 to 3.0 equivalents, preferably from 1.0 to 2.0 equivalents, based on the compound of the formula (VIII) employed.

Possible reaction temperatures are 0-75° C., preferably 15-50° C.

During the reaction, hydrogen chloride is formed which forms a compound of the formula (IX), i.e. the hydrochloride of the product of the formula (VI), in the reaction mixture. This product of the formula (IX) can either be isolated as HCl-containing product and be cleaved by addition of base to the product of the formula (VI), or it can be cleaved by addition of base even before the isolation, so that the product of the formula (VI) is isolated directly.

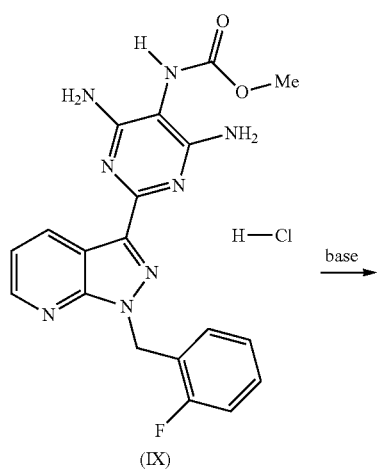

(IX)

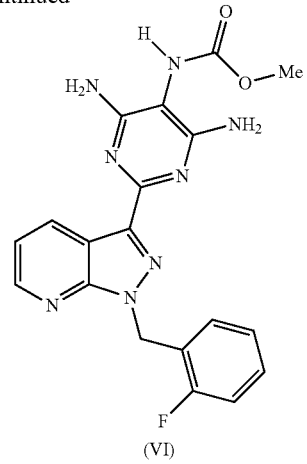

(VI)

According to the invention, it is preferred to cleave the product of the formula (IX) by addition of the base prior to the isolation and to isolate the free base of the formula (VI) directly.

According to the invention, suitable bases are all bases having a pKB which is higher than that of the compound of the formula (I). Examples which may be mentioned are: hydroxides, carbonates and phosphates of the alkali metals and alkaline earth metals, nitrogen-containing organic bases, such as trialkylamines, guanidines or amidines. Examples which may be mentioned are: lithium hydroxide, sodium hydroxide, potassium hydroxide, rubidium hydroxide, caesium hydroxide, magnesium hydroxide, calcium hydroxide, strontium hydroxide, barium hydroxide, lithium carbonate, sodium carbonate, potassium carbonate, rubidium carbonate, caesium carbonate, magnesium carbonate, calcium carbonate, strontium carbonate and barium carbonate, sodium phosphate and potassium phosphate, trialkylamines having straight-chain, cyclic or branched $C_1$-$C_{20}$-alkyl radicals, and cyclic or open-chain guanidines or amidines. Preference according to the invention is given to triethylamine, tripropylamine, diisopropylethylamine, tributylamine, dicyclohexylethylamine, cyclohexyldimethylamine, cyclohexyldiethylamine, triisooctylamine, tridecylamine, tridodecylamine, trihexadecylamine, N-methylmorpholine, DBU, DBN, tetramethylguanidine, etc. Particular preference is given to triethylamine, tributylamine, diisopropylethylamine, N-methylmorpholine, DBU, DBN.

The amount of base is from 1.0 to 2.0 equivalents, preferably from 1.0 to 1.5 equivalents, based on the methyl chloroformate of the formula (V) employed.

Possible reaction temperatures for the reaction with the base are 0-100° C., preferably 15-70° C.

The product of the formula (VI) is present in suspension and is isolated by filtration. It is washed with the $C_1$-$C_4$-alcohol and dried under reduced pressure in a customary manner.

Reaction of the Compound of the Formula (VIII) with Dimethyl Dicarbonate (X)

In a further process according to the invention, the product of the formula (VIII) is reacted with dimethyl dicarbonate of the formula (X) to give the product of the formula (VI). This reaction does not require any base such as, for example, pyridine.

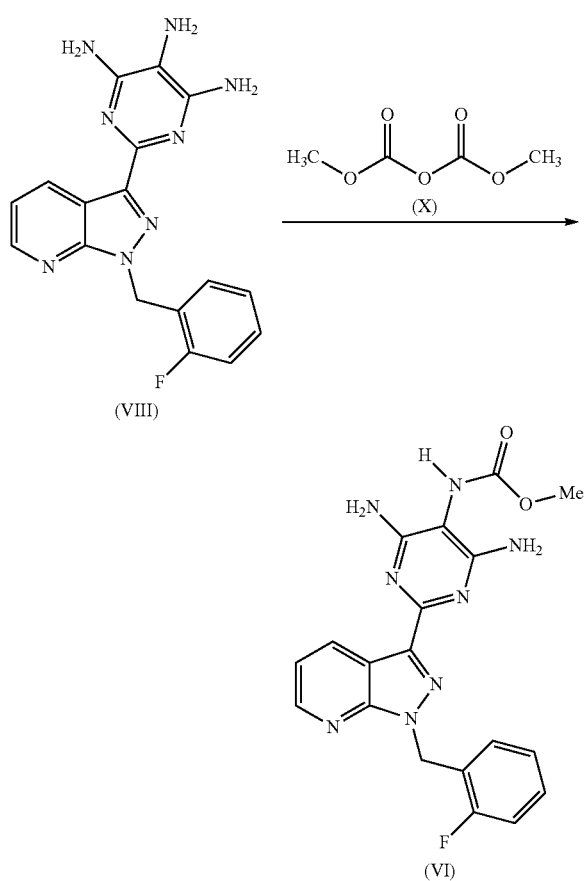

(VIII)

the product of the formula (VI), it does not decompose completely, and clearly noticeable solvent residues, i.e., for example, of the $C_1$-$C_4$-alcohol in question, thus remain in the product of the formula (VI). On the other hand, the product of the formula (VI) must not be dried at temperatures which are too hot, since it may decompose with formation of byproducts at temperatures which are too high.

Accordingly, according to the invention it is preferred to dry the product of the formula (VI) from the cleavage of the hydrochloride of the formula (IX) with base or from the direct synthesis with dimethyl dicarbonate at a product temperature of not more than 110°, particularly preferably at a product temperature of not more than 100°. Here, it is particularly preferred for any residues of $C_1$-$C_4$-alcohol present as solvate to remain in the product of the formula (VI) and to use the product of the formula (VI) in this form for preparing the intermediate of the formula (II) or the product of the formula (I). According to the invention, with very particular preference, the product of the formula (VI) contains isopropanol as residual solvent in a range of from 0 to 13%.

Methylation of the Compound of the Formula (VI)

The product of the formula (VI) obtained in this manner is reacted in a manner known per se, for example in accordance with one of the descriptions in WO 03/0945451 or ChemMedChem 2009, 4, 853-865, with a methylating agent Me-X to give a crude product which contains high amounts of the compound of the formula (I).

The solvents used for this reaction are $C_1$-$C_4$-alcohols, preferably ethanol, methanol, isopropanol, particularly preferably isopropanol.

The amount of dimethyl dicarbonate is from 1.0 to 3.0 equivalents, preferably from 1.0 to 2.0 equivalents, based on the compound of the formula (VIII) employed.

Possible reaction temperatures are 0-65° C., preferably 15-40° C.

The product of the formula (VI) precipitates and is isolated by filtration. It is washed with the $C_1$-$C_4$-alcohol and dried under reduced pressure in a customary manner.

In the reaction with dimethyl dicarbonate, the product of the formula (VI) is obtained directly. Further addition of base is therefore not required.

Both processes, i.e. the reaction of the compound of the formula (VIII) with methyl chloroformate and subsequent cleavage of the hydrochloride of the formula (IX) with base or the reaction of the compound of the formula (VIII) with dimethyl dicarbonate afford a comparable quality of the product of the formula (VI), so that the products of the formula (VI) from the two processes can be used in the same manner for the further conversion into the product of the formula (I).

Both processes are preferred according to the invention.

The compound of the formula (VI) can form solvates or solvent-containing solid forms, for example methanol-, ethanol-, or isopropanol-containing solid forms. It is therefore possible, that, when the hydrochloride of the formula (IX) is cleaved to the product of the formula (VI) or when the product of the formula (VI) is synthesized directly with dimethyl dicarbonate, a solvate of the $C_1$-$C_4$-alcohol used as solvent is obtained. The solvate may be so stable that, during drying of

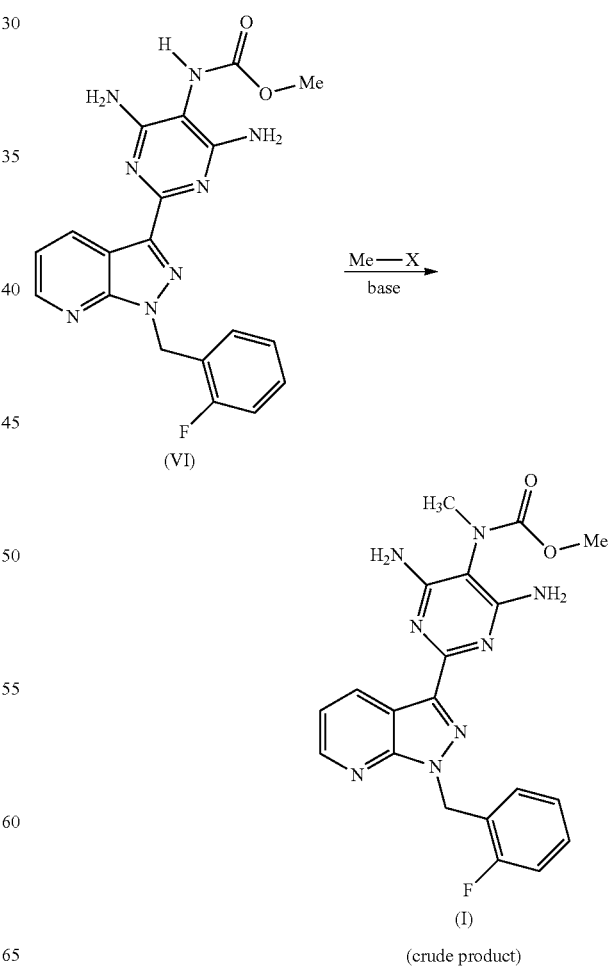

The methylating agent Me-X used in accordance with the invention is methyl iodide, dimethyl sulphate, methyl toluenesulphonate, etc., and methyl iodide or dimethyl sulphate is preferred.

Purification of the Crude Product of the Compound of the Formula (I)

According to the invention, the crude product of the formula (I) is purified for use as pharmaceutically active compound. To this end, initially, a mixture is formed which contains high amounts of the compound of the formula (II) as intermediate.

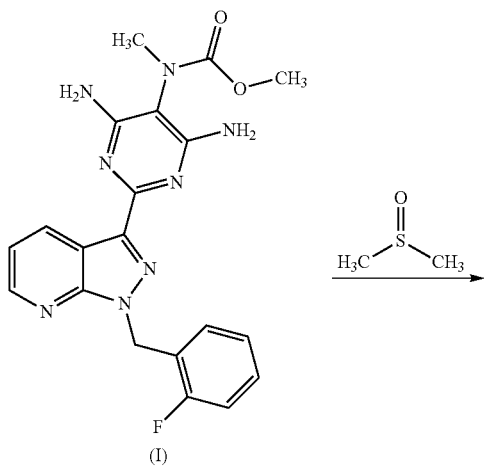

(I)
(crude product)

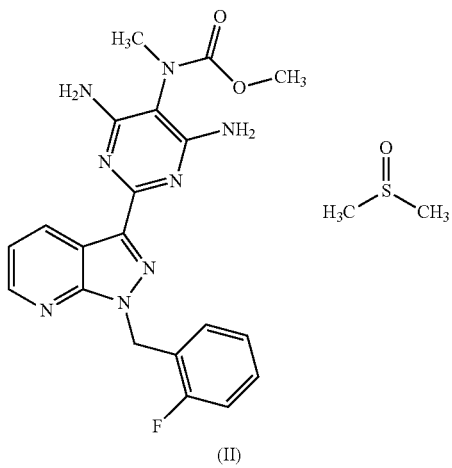

(II)

To this end, the crude product of the formula (I) is dissolved in DMSO, if appropriate in the presence of a pharmaceutically acceptable simple solvent from the class of the ketones, ethers, esters or alcohols. Examples of such solvents which may be mentioned are: methanol, ethanol, isopropanol, 1-butanol, 2-butanol, ethyl acetate, isopropyl acetate or propyl acetate, butyl acetate, tert-butyl methyl ether, diisopropyl ether, acetone, methyl ethyl ketone, methyl isobutyl ketone, etc. Preference is given to ethanol, isopropanol, ethyl acetate, isopropyl acetate, butyl acetate, methyl ethyl ketone, methyl isobutyl ketone; particular preference is given to ethyl acetate. It is also possible to use mixtures of these solvents.

DMSO is added in an amount of from 100 to 750% by weight, preferably from 150 to 500% by weight, based on the amount of the crude product of the formula (I) employed.

If appropriate, activated carbon may be added to this mixture in an amount of from 0.25 to 35% by weight, preferably from 0.5 to 20% by weight, based on the amount of the crude product of the formula (I) employed.

To form a solution, the mixture is heated to 40-120° C., preferably 50-100° C.

To form a pharmaceutically acceptable product of the formula (I), the solution has to be filtered. The filtration has to be carried out independently of whether activated carbon was added or not.

The amount of the pharmaceutically acceptable solvent which, in addition to DMSO, is added to the solution of the crude product of the formula (I), i.e. used prior to the filtration, is from 25 to 200% by weight, preferably from 40 to 100% by weight, based on the DMSO.

The filtration is carried out hot, the temperatures are 40-120° C., preferably 50-100° C.

After the filtration, a pharmaceutically acceptable solvent, preferably the same solvent as above, is added to the hot filtrate. This results in a crystallization of the product of the formula (II).

The total amount of solvent added before and after the filtration is from 200 to 1500% by weight, preferably 400-1200% by weight, based on the DMSO.

The addition temperature is 30-110° C., preferably 35-90° C.

Prior to the isolation of the solid which contains high amounts of the compound of the formula (II), to bring the precipitation to completion, the mixture is cooled to a temperature range of 0-35° C., preferably to an ambient temperature of, for example, 20-30° C.

The isolation is carried out using customary isolation devices such as a Nutsche filter or a centrifuge. To remove the mother liquor, the isolated material is, during isolation, washed with a pharmaceutically acceptable solvent, the same solvent as above being preferred.

After the DMSO redissolution, the isolated material contains high amounts of the product of the formula (II). In addition, small amounts of the product of the formula (I) may also usually precipitate directly without forming a solvate with DMSO. Also possible is the formation of solvates of a different stoichiometry or the formation of solvent adducts with no fixed stoichiometry. Moreover, DMSO may also be present in unbound form as an adhering residual solvent. The content of DMSO in the isolated material is usually from 10 to 25% by weight, preferably 12-17%. According to the invention, the product of the formula (II) is particularly preferably formed in the form of this mixture and used for preparing the purified product of the formula (I).

The product of the formula (II) obtained in this manner can now be dried or, alternatively, be used in moist form comprising solvent residues, i.e. adhering DMSO and the precipitation solvent(s), for conversion into the purified product of the formula (I).

The compound of the formula (II) is novel. It can be prepared in pure form as described in the working examples below and be characterized analytically.

For pharmaceutical use, the DMSO has to be removed from the product of the formula (II) or the mixture comprising high amounts of the compound of the formula (II).

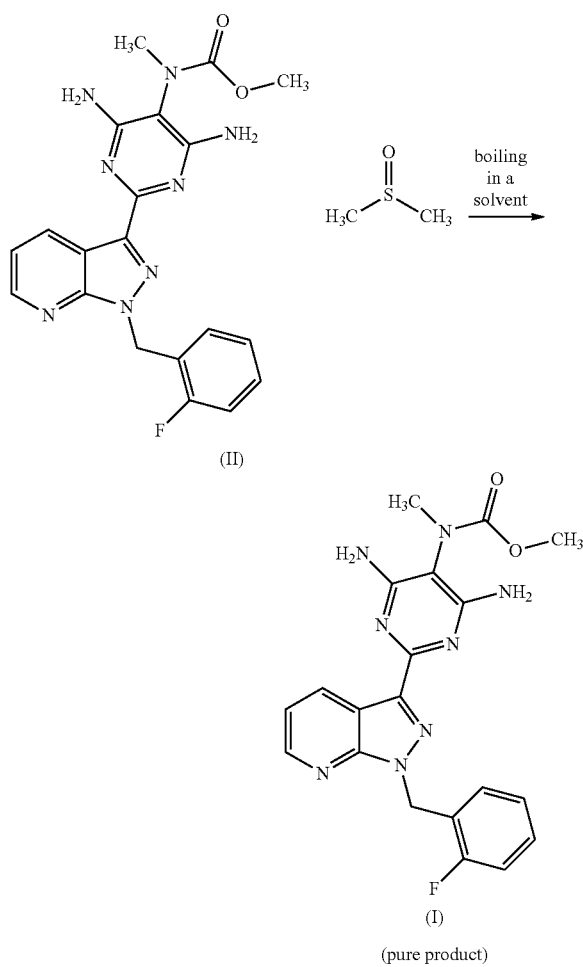

To this end, the product of the formula (II) or the isolated mixture comprising high amounts of the product of the formula (II) is boiled in a pharmaceutically acceptable solvent from the class of the ketones, ethers, esters or alcohols. Examples of such solvents which may be mentioned are: methanol, ethanol, isopropanol, 1-butanol, 2-butanol, ethyl acetate, isopropyl acetate or propyl acetate, butyl acetate, tert-butyl methyl ether, diisopropyl ether, acetone, methyl ethyl ketone, methyl isobutyl ketone, etc. Preference is given to ethanol, isopropanol, ethyl acetate, isopropyl acetate, butyl acetate, methyl ethyl ketone, methyl isobutyl ketone. It is also possible to use mixtures of these solvents. Particular preference is given to ethyl acetate or a mixture of ethyl acetate with ethanol.

Boiling takes place at reflux of the solvent in question or, if appropriate, at slightly elevated pressure. The temperature is 50-150° C., preferably 80-120° C.

The process according to the invention offers marked advantages compared to the prior art. Surprising was in particular that the direct isolation of the compound of the formula (VIII) (free base) without intermediate formation of the compound of the formula (IV) (trihydrochloride) allowed the yield to be increased markedly, with a simultaneous markedly more simple industrial practice (no acid-proof parts of the plant).

The compound of the formula (VIII) can then be converted in novel pyridine-free processes with methyl chloroformate or dimethyl carbonate into the compound of the formula (VI).

These novel processes are very simple and can be carried out with minimum expense in industry. After the reaction, the product of the formula (VI) is present suspended as a solid and can be isolated without evaporation steps by filtration. The yield obtained is very high.

It is furthermore surprising that the purification of the crude product of the formula (I) for pharmaceutical use takes place in particular by redissolution in a DMSO-containing solvent mixture and that the novel compound of the formula (II) is obtained as an intermediate in this step, if appropriate in a mixture in high proportions. By this step, all impurities are removed except for small residual amounts, so that, after the DMSO content has been removed by simple boiling, a highly pure solid of the formula (I) remains. This solid is generally colourless to very slightly yellow and the analytical purity (HPLC) is markedly above 98% by weight, which is very advantageous for pharmaceutical use.

The process can be carried out safely technically and allows a production on an industrial scale. It can be adapted flexibly to existing apparatus in the plant. In a particularly preferred embodiment, in the purification of the crude product of the formula (I), the intermediate isolation of the product of the formula (II) or of the mixture comprising high amounts of the compound of the formula (II) is carried out in a Nutsch filter dryer. Subsequent removal of the DMSO from the product of the formula (II) isolated as an intermediate in the Nutsch filter dryer is carried out by direct addition of solvent to the Nutsch filter dryer with or without intermediate drying of the product of the formula (II). This avoids open handling of the solid of the product of the formula (II) with the associated risk of contamination.

EXPERIMENTAL PART

Abbreviations and Acronyms:
abs. absolute
cat. catalytic
CI chemical ionization (in MS)
d day(s)
TLC thin-layer chromatography
DMF dimethylformamide
DMSO dimethyl sulphoxide
ee enantiomeric excess
EI electron-impact ionization (in MS)
ent enantiomer/enantiomerically pure
eq equivalent(s)
ESI electrospray ionization (in MS)
GC-MS gas chromatography-coupled mass spectrometry
% by weight percent by weight
h hour(s)
HPLC high-pressure, high-performance liquid chromatography
conc. concentrate
LC-MS liquid chromatography-coupled mass spectrometry
min minute(s)
MS mass spectrometry
NMR nuclear magnetic resonance spectrometry
Ph phenyl
$R_f$ retention index (in TLC)
$R_t$ retention time (in HPLC)
RT room temperature
v/v volume-to-volume ratio (of a solution)
aq. aqueous, aqueous solution
The examples below illustrate the invention, but the invention is not limited to the examples.

EXAMPLE 1

Preparation of 2-[1-(2-fluorobenzyl)-1H-pyrazolo[3,4-b]pyridin-3-yl]-4,5,6-pyrimidine-triamine (VIII)

In a pressure autoclave, 1100 g of the compound of the formula (III) were suspended in 5.4 l of DMF. 44 g of a conventional water-moist (about 50%) 5% Pd/carbon catalyst were added, and the sealed autoclave was, after inertization with nitrogen and application of hydrogen, hydrogenated at a hydrogen pressure of 65 bar and an internal temperature of about 60° C. for about 18 h. After cooling to about 25° C., venting and inertization, the autoclave content was removed, rinsing with 650 ml of DMF.

Three of such reactions carried out in the same manner were combined, the old catalyst was filtered off, the filtercake was rinsed with 1.1 l of DMF and the filtrate was concentrated under reduced pressure to about one third of its mass. Successively, 8.25 l of methanol and 8.25 l of water were metered into the residue of about 6.5 kg, to bring the crystallization to completion, the suspension was cooled to about 5° C. and the solid was filtered off and washed with methanol/water (1:1 vol). The product was dried at 50° C. under reduced pressure. The weight was 2415 g, which corresponds to 91.8% of theory. The content of the target product of the formula (VIII) (free base) was >98 area % or >97% by weight. The most significant impurities were DMF (about 0.8% by weight) and water (about 0.5% by weight).

EXAMPLE 2

Preparation of methyl 4,6-diamino-2-[1-(2-fluorobenzyl)-1H-pyrazolo[3,4-b]pyridin-3-yl]-5-pyrimidinylcarbamate (VI)

3063 g of the compound of the formula (VIII) and 30.7 l of technical grade isopropanol were initially charged in a reaction vessel. With stirring, 1641 g of dimethyl dicarbonate were metered in at 20-25° C., and the mixture was stirred at this temperature for 22 h. The precipitated product was filtered off with suction, washed with industrial grade isopropanol and dried at 50° C. under reduced pressure. The weight of the product obtained was 3748 g or 105.9% of theory. The product of the formula (I) contained, inter alia, about 4.7% of isopropanol virtually unremovable by drying (partially, an isopropanol solvate was present), and the analytical content was 89.5% by weight (HPLC). Based on this content, the yield was 94.8% of theory.

EXAMPLE 3

Preparation of 2-[1-(2-fluorobenzyl)-1H-pyrazolo[3,4-b]pyridin-3-yl]-4,5,6-pyrimidine-triamine (VIII)

In a pressure autoclave, 300 g of the compound of the formula (III), 1600 ml of DMF and 60 g of water-moist Raney nickel were initially charged and, after inertization, hydrogenated at an internal temperature of 60° C. and a hydrogen pressure of 65 bar for about 18 h. After cooling and venting, the old catalyst was filtered off and rinsed with 100 ml of DMF. The filtrate was concentrated under reduced pressure to 534.5 g, and at 35-40° C., 750 ml of methanol and then, after cooling, at 0-5° C., 750 ml of water were metered into the residue. The solid was filtered off and dried at 50° C. under reduced pressure. The weight was 219.7 g or 91.8% of theory.

EXAMPLE 4

Preparation of methyl 4,6-diamino-2-[1-(2-fluorobenzyl)-1H-pyrazolo[3,4-b]pyridin-3-yl]-5-pyrimidinylcarbamate (VI)

In a reaction vessel, 1.50 kg of the compound of the formula (VIII) were initially charged in 14.25 l of isopropanol, and the mixture was heated with stiffing to 35° C. 531 g of methyl chloroformate were, at a steady rate, metered in over a period of 30 min, rinsing with 750 ml of isopropanol, and the mixture was stirred at 35° C. for 16 h. The mixture was then heated to 50° C. and 3.85 l of methanol and 606 g of triethylamine were metered in with stirring at 50° C., rinsing with 450 ml of methanol. The mixture was then stirred at 50° C. for 1 h, cooled to RT and stirred at RT for 1 h. The suspended solid was filtered off with suction, washed twice with in each case 3.0 l of isopropanol/methanol (4:1) and once with 3.0 l of isopropanol and sucked dry. The moist product was dried at 50° C. for 1 h and then at 100° C. for 22 h in a vacuum drying cabinet. The weight of the product obtained was 1.793 kg or 103.3% of theory. The product of the formula (VI) contained 6.45% of isopropanol virtually unremovable by drying (partially, an isopropanol solvate was present), and the analytical content was 87.9% by weight (HPLC). Based on this content, the yield was 90.8% of theory.

COMPARATIVE EXAMPLE 5

Preparation of methyl 4,6-diamino-2-[1-(2-fluorobenzyl)-1H-pyrazolo[3,4-b]pyridin-3-yl]-5-pyrimidinyl(methyl)carbamate (I)

(Methylation in a Manner Known Per Se in Accordance with WO 03/095451, Example 8 Second Procedure)

At 20-25° C., 1630 g of the compound of the formula (VI) was suspended in 16.3 l of THF. The suspension was cooled to from −6 to −4° C., and 3480 g of a 1M solution of bis(trimethylsilyl)sodium amide were metered in. The mixture was stirred, 596 g of methyl iodide were metered in, the mixture was stirred briefly and slowly allowed to warm to about 5° C. The mixture was stirred at this temperature until the reaction had ended (about 4 h). The reaction mixture was washed 4 times with 4.1 l of 15% strength ammonium chloride solution. The organic phase was concentrated by evaporation to a residue of about 6.4 kg, and the temperature was adjusted to about 25° C. The precipitated solid was filtered off, washed with a total of 3 l of THF and dried at 50° C. under reduced pressure. This gave 1112 g of the crude product of the formula (I). This corresponded to a yield of 75.2% of theory.

EXAMPLE 6

Preparation of a mixture consisting of methyl 4,6-diamino-2-[1-(2-fluorobenzyl)-1H-pyrazolo[3,4-b]pyridin-3-yl]-5-pyrimidinylmethyl)carbamate (I) and methyl {4,6-diamino-2-[1-(2-fluorobenzyl)-1H-pyrazolo[3,4-b]pyridin-3-yl]pyrimidin-5-yl}methylcarbamate sulphinyldimethane (II) with high amounts of the product of the formula (II)

9.0 g of a crude product of the formula (I) which had been prepared in a manner comparable to Comparative Example 5 were dissolved in 16 ml of DMSO at 100° C. (The clarification by filtration which would have been required at this point to achieve a pharmaceutically acceptable product quality was dispensed within this laboratory experiment). The mixture was then allowed to cool to 75° C., 110 ml of ethyl acetate were added and the mixture was cooled slowly to about 25° C. The precipitated solid was filtered off, washed with a total of 28 ml of ethyl acetate and dried at 50° C. under reduced pressure. The weight was 9.6 g or 90.0% of theory.

EXAMPLE 7

Preparation of purified methyl 4,6-diamino-2-[1-(2-fluorobenzyl)-1H-pyrazolo[3,4-b]pyridin-3-yl]-5-pyrimidinyl(methyl)carbamate (I)

The entire amount of the product of the formula (II) prepared in the above Example 6 was stirred in 135 ml of ethyl acetate at reflux (about 78° C.) for 1 h and cooled to about 25° C. The solid was filtered off with suction, washed with a total of 36 ml of ethyl acetate and dried under reduced pressure. The weight was 7.6 g or 93.8% of theory. The content of the product was markedly above 98% by weight (HPLC). As solvent, ethyl acetate was present in an amount of about 0.2%. The DMSO content was below 0.1%.

EXAMPLE 8

Preparation of purified methyl 4,6-diamino-2-[1-(2-fluorobenzyl)-1H-pyrazolo[3,4-b]pyridin-3-yl]-5-pyrimidinyl(methyl)carbamate (I) with intermediate isolation of a mixture comprising high amounts of methyl {4,6-diamino-2-[1-(2-fluorobenzyl)-1H-pyrazolo[3,4-b]pyridin-3-yl]pyrimidin-5-yl}methylcarbamate sulphinyldimethane (II) as moist product 193.5 g of a crude product of the formula (I) which had been prepared in a manner comparable to Comparative Example 5 were dissolved in 344 ml of DMSO and 172 ml of ethyl acetate at about 96° C. 19.4 g of activated carbon and 172 ml of ethyl acetate were then added, and the hot mixture was stirred. The hot mixture was then filtered off to remove the activated carbon, rinsing with 172 ml of ethyl acetate. The temperature of the filtrate was adjusted to 78° C., and 1850 ml of ethyl acetate were added slowly. Over about 2-3 h, the mixture was cooled to about 25° C., and the solid was filtered off and washed with a total of 772 ml of ethyl acetate. The moist product, which contained high amounts of the compound of the formula (II) in a mixture was suspended in 2900 ml of ethyl acetate, heated at reflux for 1 h and cooled to about 25° C. The solid was filtered off with suction, washed with a total of 774 ml of ethyl acetate and dried at 50° C. under reduced pressure. The weight obtained was 155.1 g or 80.2% of the starting material. The content of the product was markedly above 98% by weight (HPLC). As solvents, virtually only ethyl acetate and DMSO were present in small amounts.

EXAMPLE 9

Preparation and analytical characterization of methyl {4,6-diamino-2-[1-(2-fluorobenzyl)-1H-pyrazolo[3,4-b]pyridin-3-yl]pyrimidin-5-yl}methylcarbamate sulphinyldimethane (II)

14.8 g of a crude product of the formula (I) which had been prepared in a manner comparable to Comparative Example 5 were dissolved in 28.9 g of DMSO and 11.85 g of ethyl acetate at about 94° C. 1.5 g of activated carbon Norit A-Supra and a further 11.85 g of ethyl acetate were then added, the mixture was stirred at reflux (88-90° C.) for 1 h and the hot mixture was then filtered to remove the activated carbon. The solid, some of which had already precipitated, was re-dissolved by warming to about 78° C., and the solution was then allowed to cool slowly. The precipitated solid was filtered off with suction at RT, washed three times with in each case 50 ml of ethyl acetate and dried in a drying cabinet at 30° C. for 18 h. This gave 9.2 g or 52.5% of theory of a slightly yellowish crystal powder of the compound of the formula (II).

HPLC: 99.90 area % (without taking the DMSO into account)

DMSO (GC): 14.7% by weight $^1$H-NMR (400 MHz in DMF-$d_7$):

d=2.59 (s, about 6H, 2 $CH_3$ at DMSO), 3.13 (s, 3H, N—$CH_3$), 3.58+3.67 (two s, 3H, hindered rotation at O—$CH_3$), 5.91 (s, 2H, —$CH_2$—), 6.53 (s, 4H, 2-$NH_2$), 7.05-7.40 (m, 5H, 4 aromatic H at the o-fluorobenzyl substituent and 1H at the pyrido ring meta to the pyrido nitrogen), 8.60 (dd, 1H, at the pyrido ring ortho to the pyrido nitrogen), 9.12 (dd, 1H, at the pyrido ring para to the pyrido nitrogen).

Elemental analysis:

| found | C: 52.2% | calculated | C: 52.79% |
|---|---|---|---|
| | H: 4.9% | | H: 5.03% |
| | N: 22.7% | | N: 22.39% |

The invention claimed is:

1. A process for preparing methyl 4,6-diamino-2-[1-(2-fluorobenzyl)-1H-pyrazolo[3,4-b]pyridin-3-yl]-5-pyrimidinylcarbamate of the Formula VI:

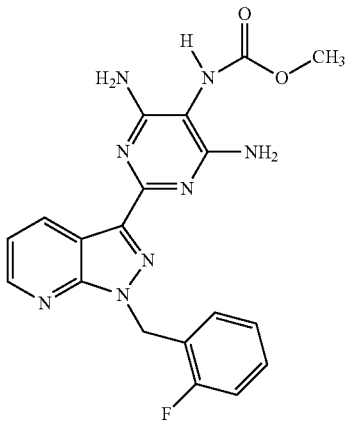

comprising reacting 2-[1-(2-fluorobenzyl)-1H-pyrazolo [3,4-b]pyridin-3-yl]-4,5,6-pyrimidinetriamine of the Formula VIII:

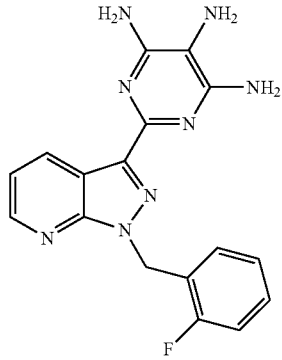

with dimethyl dicarbonate of the Formula X:

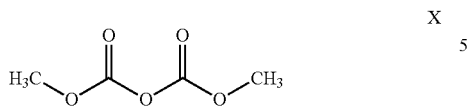

to produce methyl 4,6-diamino-2-[1-(2-fluorobenzyl)-1H-pyrazolo[3,4-b]pyridin-3-yl]-5-pyrimidinylcarbamate of the Formula VI.

2. The process of claim 1, wherein the reaction occurs without the addition of a base.

3. The process of claim 1, wherein the reaction occurs in the presence of a $C_1$-$C_4$ alcohol solvent.

4. The process of claim 1, wherein after reacting 2-[1-(2-fluorobenzyl)-1H-pyrazolo[3,4-b]pyridin-3-yl]-4,5,6-pyrimidinetriamine of Formula VIII with dimethyl dicarbonate of the Formula X, methyl 4,6-diamino-2-[1-(2-fluorobenzyl)-1H-pyrazolo[3,4-b]pyridin-3-yl]-5-pyrimidinylcarbamate of the Formula VI is isolated by filtration.

* * * * *